(12) United States Patent
Stokely et al.

(10) Patent No.: US 10,591,639 B2
(45) Date of Patent: Mar. 17, 2020

(54) METHODS AND SYSTEMS EMPLOYING A FLOW PREDICTION MODEL BASED ON ACOUSTIC ACTIVITY AND PROPPANT COMPENSATION

(71) Applicant: Halliburton Energy Services, Inc., Houston, TX (US)

(72) Inventors: Christopher Lee Stokely, Houston, TX (US); Leonardo de Oliveira Nunes, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 73 days.

(21) Appl. No.: 14/763,210

(22) PCT Filed: Oct. 17, 2014

(86) PCT No.: PCT/US2014/061167
§ 371 (c)(1),
(2) Date: Jul. 24, 2015

(87) PCT Pub. No.: WO2016/060688
PCT Pub. Date: Apr. 21, 2016

(65) Prior Publication Data
US 2016/0266276 A1 Sep. 15, 2016

(51) Int. Cl.
*E21B 47/10* (2012.01)
*E21B 47/12* (2012.01)
(Continued)

(52) U.S. Cl.
CPC ............ *G01V 99/005* (2013.01); *E21B 43/26* (2013.01); *E21B 43/267* (2013.01);
(Continued)

(58) Field of Classification Search
CPC .... G01V 11/002; G01V 11/00; G01V 99/005; G06F 17/5009; E21B 43/26;
(Continued)

(56) References Cited

U.S. PATENT DOCUMENTS 5,257,530 A * 11/1993 Beattie .................. E21B 47/101
73/61.75
2008/0149329 A1 6/2008 Cooper et al.
(Continued)

FOREIGN PATENT DOCUMENTS

CA 2841403 A1 1/2013
WO WO-2012/030814 3/2012

OTHER PUBLICATIONS

Molenaar, Menno M., et al. "First downhole application of distributed acoustic sensing for hydraulic-fracturing monitoring and diagnostics." SPE Drilling & Completion 27.01 (2012). pp. 32-38. (https://www.onepetro.org/journal-paper/SPE-140561-PA).*
(Continued)

*Primary Examiner* — Kamini S Shah
*Assistant Examiner* — John E Johansen
(74) *Attorney, Agent, or Firm* — Gilliam IP PLLC

(57) ABSTRACT

An example method includes providing source light to an optical fiber deployed in a downhole environment, receiving backscattered light from the optical fiber, and producing one or more optical interferometry signals from the backscattered light. The method also includes converting each of the one or more optical interferometry signals to an electrical signal and digitizing each electrical signal to obtain one or more digitized electrical signals. The method also includes deriving acoustic activity values as a function of time and position from the one or more digitized electrical signal. The method also includes applying at least some of the acoustic activity values to a flow prediction model to obtain a
(Continued)

predicted fluid flow as a function of time, wherein the flow prediction model includes a proppant compensation value or factor. The method also includes storing or displaying the predicted fluid flow.

20 Claims, 7 Drawing Sheets

(51) Int. Cl.

| | | |
|---|---|---|
| *G01N 21/17* | (2006.01) | |
| *G01N 21/01* | (2006.01) | |
| *E21B 43/26* | (2006.01) | |
| *G01V 99/00* | (2009.01) | |
| *G01V 11/00* | (2006.01) | |
| *G01N 21/45* | (2006.01) | |
| *E21B 43/267* | (2006.01) | |
| *E21B 47/00* | (2012.01) | |
| *E21B 47/06* | (2012.01) | |

(52) U.S. Cl.
CPC ............ *E21B 47/101* (2013.01); *E21B 47/12* (2013.01); *G01N 21/01* (2013.01); *G01N 21/1702* (2013.01); *G01N 21/45* (2013.01); *G01V 11/00* (2013.01); *G01V 11/002* (2013.01); *E21B 47/00* (2013.01); *E21B 47/06* (2013.01); *E21B 47/065* (2013.01); *E21B 47/123* (2013.01)

(58) Field of Classification Search
CPC ...... E21B 43/267; E21B 47/101; E21B 47/12; E21B 47/00; E21B 47/065; E21B 47/06; E21B 47/123; G01N 21/45; G01N 21/1702; G01N 21/01
USPC ....................................................... 703/2, 10
See application file for complete search history.

(56) References Cited

U.S. PATENT DOCUMENTS

| | | | | |
|---|---|---|---|---|
| 2009/0288820 | A1* | 11/2009 | Barron | B01J 13/02 166/249 |
| 2010/0207019 | A1 | 8/2010 | Hartog et al. | |
| 2012/0018149 | A1 | 1/2012 | Fidan et al. | |
| 2012/0112072 | A1* | 5/2012 | Jones | G01N 21/359 250/339.07 |
| 2013/0233537 | A1* | 9/2013 | McEwen-King | E21B 43/26 166/250.1 |
| 2013/0342210 | A1 | 12/2013 | Stokely | |
| 2014/0076569 | A1* | 3/2014 | Pham | E21B 43/267 166/305.1 |
| 2015/0144333 | A1 | 5/2015 | Lee et al. | |
| 2015/0233226 | A1* | 8/2015 | Holzhauser | E21B 43/267 166/280.1 |
| 2016/0146962 | A1* | 5/2016 | Hayward | E21B 43/26 166/250.1 |
| 2016/0265345 | A1* | 9/2016 | In 'T Panhuis | E21B 47/123 |

OTHER PUBLICATIONS

Molenaar, Mathieu M., and Barbara E. Cox. "Field cases of hydraulic fracture stimulation diagnostics using fiber optic distributed acoustic sensing (DAS) measurements and Analyses." SPE Unconventional Gas Conference and Exhibition. Society of Petroleum Engineers, 2013. SPE 164030. pp. 1-10. (Year: 2013).*
Van Der Horst, Juun, et al. "Fiber Optic Sensing for Improved Wellbore Surveillance." IPTC 2013: International Petroleum Technology Conference. IPTC 16873. 2013. pp. 1-6. (Year: 2013).*
Johannessen, Kjetil, Brian Keith Drakeley, and Mahmoud Farhadiroushan. "Distributed Acoustic Sensing—a new way of listening to your well/reservoir." SPE Intelligent Energy International. Society of Petroleum Engineers, 2012. SPE 149602. pp. 1-9. (Year: 2012).*
Molenaar, Mathieu M., and Barbara E. Cox. "Field cases of hydraulic fracture stimulation diagnostics using fiber optic distributed acoustic sensing (DAS) measurements and Analyses." SPE Unconventional Gas Conference and Exhibition. Society of Petroleum Engineers, 2013. SPE 164030. pp. 1-10. (Year: 2013).*
Van Der Horst, Juun, et al. "Fiber Optic Sensing for Improved Wellbore Surveillance." IPTC 2013: International Petroleum Technology Conference. IPTC 16873. 2013. pp. 1-6. (Year: 2013).*
Johannessen, Kjetil, Brian Keith Drakeley, and Mahmoud Farhadiroushan. "Distributed Acoustic Sensing—a new way of listening to your well/reservoir." SPE Intelligent Energy International. Society of Petroleum Engineers, 2012. SPE 149602. pp. 1-9. (Year: 2012).*
"International Search Report & Written Opinion" dated Jun. 30, 2015, "Methods and Systems Employing a Flow Prediction Model Based on Acoustic Activity and Proppant Compensation", Appl. No. PCT/US2014/061167 filed Oct. 17, 2014, 10 pgs.
Bhongale, Satyan G. et al., "Downhole Sensing Systems and Methods Employing Squeezed Light Interferometry", Appl. No. PCT/US2014/019231 filed Feb. 28, 2014, 18 pgs.
Bhongale, Satyan G. et al., "Downhole Sensing Using Parametric Amplification with Squeezed or Entangled Light for Internal Mode Input", Appl. No. PCT/US2014/031372 filed Mar. 20, 2014, 21 pgs.
Nunes, Leonardo D. et al., "Distributed Sensing Systems and Methods with Efficient Energy Spectrum Analysis", Appl. No. PCT/US2014/047141 dated Jul. 18, 2014, 30 pgs.
Ellmauthaler, Andreas et al., "Distributed Sensing Systems and Methods with I/Q Data Balancing Based on Ellipse Fitting", Appl. No. PCT/US2014/048798 filed Jul. 30, 2014, 33 pgs.
Stokely, Christopher L. et al., "Systems and Methods for Spread Spectrum Distributed Acoustic Sensor Monitoring", Appl. No. PCT/US2013/054588 filed Aug. 12, 2013, 35 pgs.
Nunes, Leonardo D. et al., "Systems and Methods for Multiple-Code Continuous-Wave Distributed Acoustic Sensing", Appl. No. PCT/US2014/012284 filed Jan. 21, 201, 48 pgs.
CA Application Serial No. 2,961,720, Examiner's Requisition, dated Apr. 25, 2018, 6 pages.
Canadian Application Serial No. 2,961,720; Office Action, dated Jan. 23, 2019, 3 pages.

* cited by examiner

METHODS AND SYSTEMS EMPLOYING A FLOW PREDICTION MODEL BASED ON ACOUSTIC ACTIVITY AND PROPPANT COMPENSATION

BACKGROUND

In the search for hydrocarbons and development of hydrocarbon-bearing wells, hydraulic fracturing is a common technique to improve hydrocarbon recovery. Hydraulic fracturing involves injecting a high-pressure fluid into a wellbore to create or expand cracks in the subsurface formations so that natural gas and petroleum can flow more freely. Sometimes proppants (e.g., sand or aluminum oxide) are added to the fracturing fluid and remain in the fractures to hold them open to some degree when the hydraulic pressure is reduced and thus improve fluid flow through the fractures.

It may be difficult to determine whether a fracture downhole is operating as intended or if a flow rate through a given perforation cluster is as expected without a significant interruption of downhole operations and use of expensive and time-consuming equipment. For example, deployment of a wireline logging tool to collect flow rate data would interrupt and/or delay other downhole operations. Even if more permanent installations of flow rate sensors downhole were possible, distributing multiple sensors in a way that effectively monitors flow near different perforation clusters would be costly and tedious.

Most wells are not instrumented with anything more than a surface and/or downhole pressure meter. Downhole flow estimation is highly uncertain when using only pressure data and a model of the reservoir. There are commercial downhole flowmeters available but they suffer from technical limitations regarding placement in the wellbore, orientation, and acceptable flow rates. During hydraulic fracturing, the flow rates are so large (50,000-70,000 barrels per day) that mechanical flow meters often do not survive, particularly when proppant is used.

Fiber optic sensing systems have been developed to monitor downhole parameters such as vibration, acoustics, pressure, and temperature. Unfortunately, efforts to correlate acoustic activity with fluid flow have thus far resulted in inaccurate estimates.

BRIEF DESCRIPTION OF THE DRAWINGS

Accordingly, there are disclosed in the drawings and the following description specific methods and systems employing flow prediction models based on acoustic activity and proppant compensation. In the drawings.

Figure 1A:
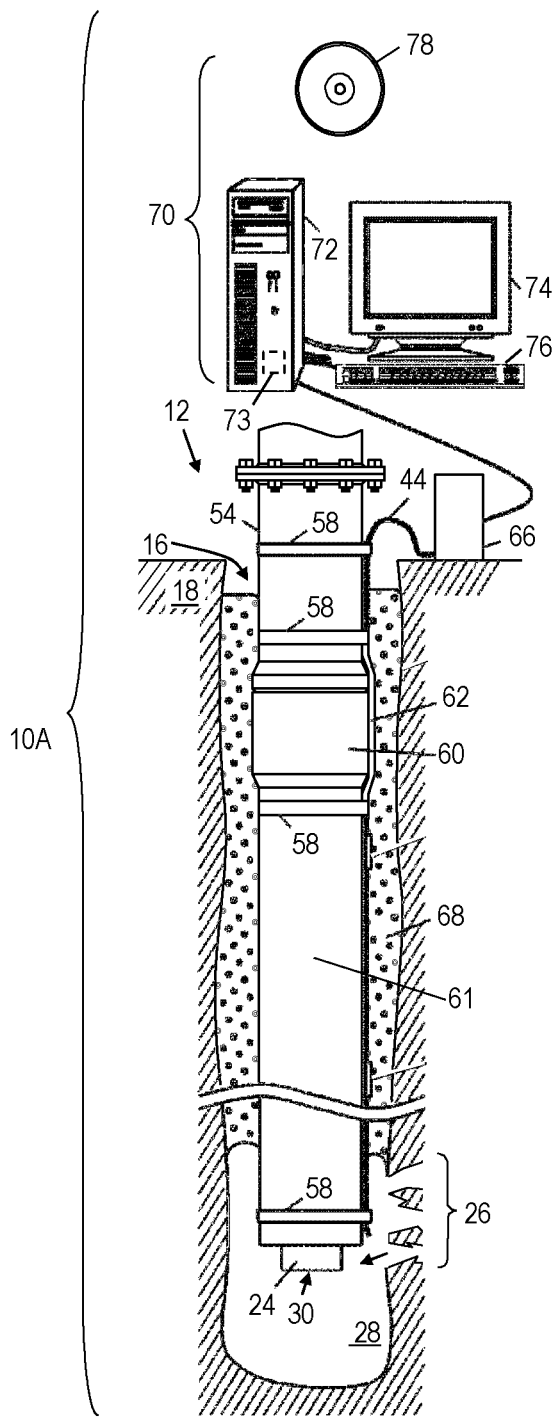
FIGS. 1A-1C are schematic diagrams of illustrative well environments with distributed sensing components.

It should be understood, however, that the specific embodiments given in the drawings and detailed description thereto do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Disclosed herein are methods and systems employing a flow prediction model based on acoustic activity and proppant compensation. In at least some embodiments, downhole acoustic activity is monitored before, during, and/or after hydraulic fracturing operations using a distributed acoustic sensing (DAS) system and/or other downhole sensors. An example DAS system involves deploying an optical fiber downhole by attaching the fiber to the outside of the casing during casing deployment and later cementing the casing (and embedding the fiber) into place. In some cases, the fiber is attached to the outside of production tubing. Acoustic activity values obtained from a DAS system or other downhole sensors are provided as input to a flow prediction model that includes a proppant compensation factor or value. The proppant compensation value or factor is intended to account for reduced acoustic activity resulting from the addition of proppants. For example, in some embodiments, the proppant compensation value or factor used with a flow prediction model may be selected based on a downhole proppant estimate and/or an acoustic attenuation estimate.

In different embodiments, the acoustic activity values input to a flow prediction model may vary. For example, the acoustic activity values input to a flow prediction model may be averaged and/or normalized as a function of time, position, and frequency. Additionally or alternatively, a flow prediction model may be calibrated. Example calibrations involve adjusting one or more variables of a flow prediction model based on a comparison of predicted fluid flow for one perforation cluster and a surface flow rate, a sum of predicted fluid flow for each of a plurality of perforation clusters with a surface flow rate, a comparison of acoustic activity values obtained with and without a surface fluid flow, and/or a comparison of acoustic activity values obtained before and after proppants are added.

In different embodiments, the predicted fluid flow output from a flow prediction model may correspond to one perforation cluster or a plurality of perforation clusters. The predicted flow rate can be stored for later analysis and/or displayed via a monitor. As an example, the predicted fluid flow may be used for turbulent flow monitoring, plug leak detection, flow-regime determination, wellbore integrity monitoring, event detection, anomalous behavior such as increases in reservoir pressure, inter-stage fluid communication, and inter-cluster fluid communication, data visualization, and decision making. In some embodiments, a computer system displays a plan based on the predicted fluid flow. The plan may correspond to well treatment operations and/or proppant injection operations. Additionally or alternatively, a computer system may generate control signals to initiate or adjust a downhole operation based on the predicted fluid flow. Example downhole operations include, for example, well treatment operations (acidization), proppant injection operations including applying diverters (spheres) or other means of closing perforation clusters or openings from the wellbore to the reservoir, and/or fracturing operations. Various acoustic activity monitoring options, flow prediction model input options, flow prediction model analysis options, flow prediction model calibration options, and use options for predicted fluid flow results are described herein.

Without limitation to other embodiments, a flow prediction model may be used to plan downhole operations and/or to dynamically direct downhole operations affected by proppants. As an example, the flow prediction model may predict whether flow through each of a plurality of perforation clusters is occurring as well as provide information regarding the flow rate for each perforation cluster. Applying a flow prediction model during hydraulic fracturing operations enables the effects of hydraulic fracturing to be monitored. Further, the effect of adding proppants, treatments, and/or diverters can be monitored. As needed, adjustments to hydraulic fracturing operations can be made based on the predicted fluid flow obtained from a flow prediction model. Further, decisions regarding future well completion operations and/or production operations may be based on the predicted fluid flow obtained from a flow prediction model.

As disclosed herein, different flow prediction models are possible. The choice of which flow prediction model to use may vary according to criteria such as the availability of particular types of data used to train, calibrate, or select model parameters. Further, it should be appreciated that switching between different flow prediction models is possible. Further, combining the results from different flow prediction models is possible. In at least some embodiments, the prediction results from one or more flow prediction models are evaluated. As needed, model parameters of one or more flow prediction models can be updated based on such an evaluation.

Figure 1B:
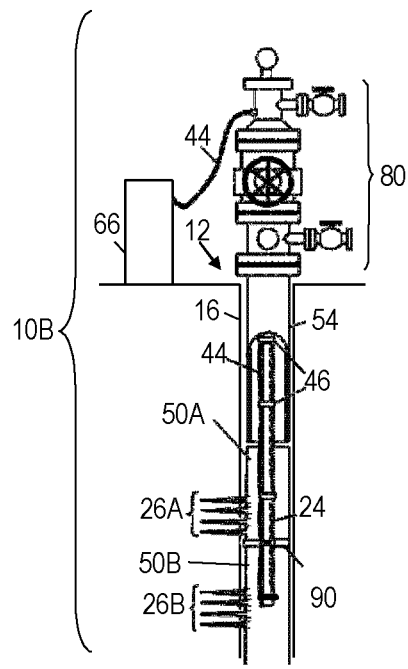
Figure 1C:
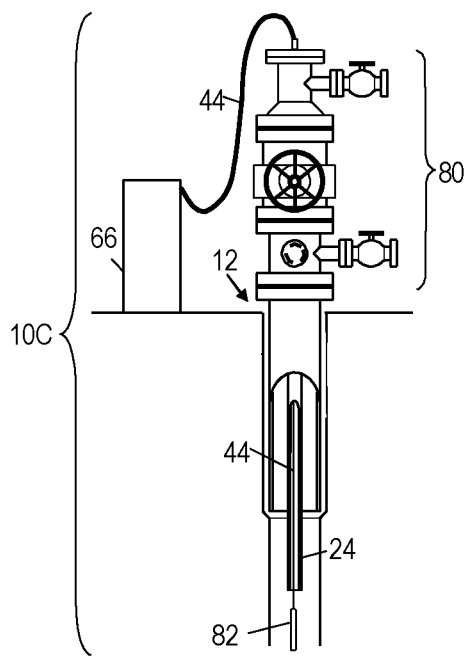

The disclosed methods and systems employing a flow prediction model based on acoustic activity and proppant compensation are best understood in an application context. Turning now to the figures, FIGS. 1A-1C show illustrative well environments 10A-10C with distributed sensing components. In well environment 10A, a rig has been used to drill and complete well 12 in a typical manner, with a casing string 54 positioned in the borehole 16 that penetrate into the earth 18. The casing string 54 includes multiple tubular casing sections 61 (usually about 30 feet long) connected end-to-end by couplings 60. Typically the casing string includes many such sections 61 and couplings 60. Within the well 12, a cement slurry 68 has been injected into the annular space between the outer surface of the casing string 54 and the inner surface of the borehole 16 and allowed to set. A production tubing string 24 has been positioned in an inner bore of the casing string 54.

The well 12 is adapted to guide a desired fluid (e.g., oil or gas) from a bottom of the borehole 16 to a surface of the earth 18. Perforations 26 have been formed at a bottom of the borehole 16 to facilitate the flow of a fluid 28 from a surrounding formation into the borehole and thence to the surface. For example, the perforations 26 are shown to be near an opening 30 at the bottom of the production tubing string 24. Note that this well configuration is illustrative and not limiting on the scope of the disclosure. For example, fluid flow to or from a formation is possible at other points along the well 12 (not only at the bottom). Further, well 12 could include horizontal sections or curved sections in addition to the vertical section represented. Further, the well 12 may correspond to a production well or injection well. In alternative embodiments, optical distributed sensing components as described herein may be deployed in a monitoring well. Such a monitoring well may be cased, but does not necessarily need a production tubing string 24 or perforations 26.

The well environment 10A includes an interface 66 coupled to a fiber optic cable 44 for distributed sensing operations. The interface 66 is located on the surface of the earth 18 near the wellhead, i.e., a "surface interface". In the embodiment of FIG. 1A, the fiber optic cable 44 extends along an outer surface of the casing string 54 and is held against the outer surface of the casing string 54 at spaced apart locations by multiple bands 58 that extend around the casing string 54. A protective covering 62 may be installed over the fiber optic cable 44 at each of the couplings 60 of the casing string 54 to prevent the fiber optic cable 44 from being pinched or sheared by the coupling's contact with the borehole wall. The protective covering 62 may be held in place, for example, by two of the bands 58 installed on either side of coupling 60.

In at least some embodiments, the fiber optic cable 44 terminates at surface interface 66 with an optical port adapted for coupling the fiber(s) in cable 44 to a light source and a detector, which when combined into a single device is also known as an interrogator. The light source transmits light pulses along the fiber optic cable 44 which contains a fiber with scattering impurities. As each pulse of light propagates along the fiber, some of the pulse is scattered back along the fiber from every point on the fiber. Thus, the entire fiber acts as a distributed sensor. The optical port of the surface interface 66 communicates backscattered light to the detector, which responsively produces interferometry measurements from backscattered light attributes (e.g., phase or phase shift) corresponding to different points along the fiber optic cable 44. From the recovered phase information, the value of a downhole parameter sensed by the fiber at the location of the backscatter can be determined. As described herein, flow prediction can be performed at least in part on recovered phase information, which represents acoustic activity levels at different points along the fiber optic cable 44.

As shown, the well environment 10A also includes a computer 70 coupled to the surface interface 66 to control the light source and detector. The illustrated computer 70 includes a chassis 72 with at least one processing unit 73. Further the computer 70 includes an output device 74 (e.g., a monitor as shown in FIG. 1A, or a printer), an input device 76 (e.g., a keyboard), and non-transient information storage media 78 (e.g., magnetic or optical data storage disks). It should be appreciated that the computer 70 may be implemented in different forms including, for example, an embedded computer permanently installed as part of the surface interface 66, a portable computer that is plugged into or wirelessly linked to the surface interface 66 as desired to collect data, and a remote desktop computer coupled to the surface interface 66 via a wireless link and/or a wired communication network. In at least some embodiments, the computer 70 is adapted to receive digitized interferometry signals from the surface interface 66 and to responsively determine a distributed sensing signal. The distributed sensing signal may correspond to a phase or phase variance as a function of time that corresponds to a distributed sensing parameter such as temperature, acoustic energy, vibrational energy (including active or passive seismic), pressure, strain, deformation, chemical concentrations, nuclear radiation intensity, electromagnetic energy, and/or acceleration. In accordance with at least some embodiments, the computer 70 employs a flow prediction model that predicts flow as a function of time and position along the fiber optic cable 44 using acoustic activity values obtained from the distributed sensing signal. As described herein, the flow prediction model includes a proppant compensation factor or value.

In at least some embodiments, the non-transient information storage media 78 stores a software program for execution by computer 70. The instructions of the software program cause the computer 70 to recover phase information from digitized interferometry signals received from surface interface 66 and to perform flow prediction operations as described herein. Further, instructions of the software program may also cause the computer 70 to display information associated with distributed sensing parameter values and flow prediction results via the output device 74. Further, instructions of the software program additionally or alternatively cause the computer 70 to generate control signals to direct surface operations or downhole operations based on flow prediction results. The generation of control signals may be with or without involvement of an operator, and may be used to direct operations that adjust proppant options, fracturing options, diverter options, etc.

FIG. 1B shows an alternative well environment 10B with distributed sensing components, where the fiber optic cable 44 is strapped to the outside of the production tubing 24 rather than the outside of casing 54. Rather than exiting the well 12 from the annular space outside the casing 54, the fiber optic cable 44 exits through an appropriate port in "Christmas tree" 80 (i.e., the assembly of pipes, valves, spools, and fittings connected to the top of the well 12 to direct and control the flow of fluids to and from the well 12) and couples to surface interface 66, which may include optical interrogation and receiver components to perform interferometry analysis of backscattered light along fiber optic cable 44 as described herein. Further, a computer (e.g., computer 70 in FIG. 1A) may receive digitized interferometry signals from surface interface 66, recover phase information, and perform flow prediction as described herein. The phase information, distributed sensing parameter values, and/or flow prediction results may be stored or displayed. Further, logs and images derived from distributed sensing parameter values and/or flow prediction results may be stored or displayed.

In the well environment 10B, the fiber optic cable 44 extends along the outer surface of the production tubing string 24 and is held against the outer surface of the production tubing string 24 at spaced apart locations by multiple bands 46 that extend around the production tubing string 24. In some embodiments, a portion of the fiber optic cable 44 (a "hanging tail") extends past the production tubing string 24. In the well environment 10B, two perforations 26A and 26B have been created in borehole 16 to facilitate obtaining formation fluids from two different zones 50A and 50B defined by a packer 90 that seals an annulus around the production tubing string 24. More specifically, formation fluid enters zone 50A and production tubing string 24 via the perforation 26A, while additional formation fluid enters zone 50B and production tubing string 24 via the perforation 26B. As shown, the fiber optic cable extends through the different zones 50A and 50B to enable distributed sensing operations along well 12 including zones 50A and 50B. Although only two zones 50A and 50B are shown for optical distributed sensing well environment 10B, it should be appreciated that additional zones may be defined along well 12.

FIG. 1C shows an alternative well environment 10C with distributed sensing components, where the fiber optic cable 44 is suspended inside production tubing 24. A weight 82 or other conveyance mechanism is employed to deploy and possibly anchor the fiber optic cable 44 within the production tubing 24 to minimize risks of tangling and movement of the fiber optic cable 44 from its desired location. The fiber optic cable 44 exits the well 12 via an appropriate port in Christmas tree 80 and attaches to the surface interface 66. Again, surface interface 66 and a computer (e.g., computer 70 in FIG. 1A) enables interferometry analysis of backscattered light along fiber optic cable 44, recovery of phase information, and flow prediction operations as described herein. Other alternative well environments with distributed sensing components employ composite tubing with one or more optical fibers embedded in the wall of the tubing. The composite tubing can be employed as the casing and/or the production string.

Figure 2:
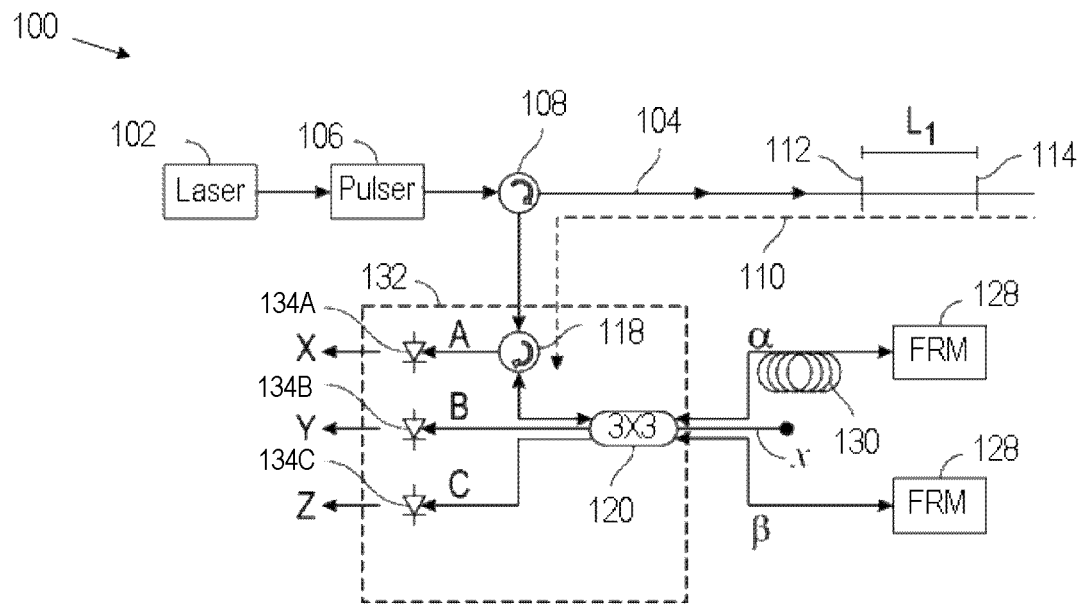
FIG. 2 is a schematic diagram of an illustrative optical phase interferometric sensing arrangement.

FIG. 2 depicts one illustrative arrangement 100 for optical phase interferometric sensing of backscattered light. There are various forms of backscattering. Rayleigh backscattering has the highest intensity and is centered at the wavelength of the source light. Rayleigh backscattering is due to microscopic inhomogeneities of refractive index in the waveguide material matrix. Brillouin and Raman backscattering are other types of detectable backscattering. Raman backscattering (which is due to thermal excited molecular vibration known as optical phonons) has an intensity which varies with temperature T, whereas Brillouin backscattering (which is due to thermal excited acoustic waves known as acoustic phonons) has a wavelength which varies with both temperature T and strain E. As desired, a particular type of backscattered light may be sampled many times and averaged, which results in an effective sample rate of from tens of seconds to several minutes, depending on the desired signal-to-noise ratio, fiber length, and desired accuracy.

The arrangement 100 includes a laser 102 or other light source that generate an interrogation signal on a distributed sensing fiber 104. The laser 102 may provide a pulsed or non-pulsed interrogation signal. If a non-pulsed interrogation signal is output from the laser 102, a pulser 106 may be employed to pulse the interrogation signal. The interrogation signal may then interact with a first circulator 108 which couples the pulsed interrogation signal to the distributed sensing fiber 104. As each interrogation signal pulse travels through the distributed sensing fiber 104, a portion of the pulse energy is reflected due to reflective elements or imperfections along the distributed sensing fiber 104.

For illustrative purposes, the reflected signal is depicted in FIG. 2 as return signal 110. In some embodiments, the return signal 110 may be generated from discrete reflective elements placed along the distributed sensing fiber 104, such as fiber Bragg gratings (FBGs) arranged at positions 112 and 114. Alternatively, when performing distributed acoustic sensing (DAS), the return signal 110 may be generated from reflections within the distributed sensing fiber 104 due to fiber imperfections (e.g., impurities). In FIG. 2, backscatter or reflection occurs at the positions 112 and 114 along the distributed sensing fiber 104. However, those of skill in the art will recognize that there may be numerous other reflection points along the distributed sensing fiber 104.

The first circulator 108 additionally couples the return signal 110 to a receiver 132. In at least some embodiments, the receiver 132 includes a second circulator 118 which conveys the return signal 110 to a 3×3 fiber optic coupler 120. The fiber optic coupler 120 distributes the return signal 110 across three paths labeled α, β, and x. The x path is terminated with an absorber and is not used further. The α and β paths are each terminated with a Faraday rotator mirror (FRM) 128 that reflects the signals back to the fiber optic coupler 120, albeit with a polarization reversal that compensates for any polarization shifts inadvertently introduced along the α and β paths. A delay coil 130 is included in the α path to introduce a delay in the reflected signal relative to the signal reflected along the β path. The fiber optic coupler 120 combines the signals from the α and β (and the unused x) paths to form three optical interferometry signals A, B, C. The delay introduced between the α and β paths corresponds to the distance or "sensing window" L1 between the reflection points 112, 114 on the distributed sensing fiber 104, enabling the phase change incurred over this length to be measured and monitored as an interferometric signal phase. Due to the nature of the fiber optic coupler 120, the optical interferometry signals A, B, C have mutual phase separations of 120°. For example, as the α and β signals enter the 3×3 coupler 120, the interferometric signal A exiting the fiber optic coupler 120 may be α+β<0°, B may be α+(β<+120°, and C may be α+(β<−120°.

The optical phase interferometric sensing arrangement 100 also implements single-ended detectors 134A-134C, which receive the optical interferometry signals A, B, and C and output signals X, Y, and Z. Examples of single-ended detectors 134A-134C include p-intrinsic-n field-effect-transistors (PINFETs), where optical receivers and high-gain transimpedance amplifiers are used. In at least some embodiments, the single-ended detectors 134A-134C correspond to square law detectors with a bandwidth much lower than the optical frequency (e.g., less than 1 GHz). In an exemplary operation, measurements such as dynamic strain, acoustics, and vibrations may be determined through analysis of the outputs of the single-ended detectors 134A-134C to determine the associated optical phase shift. For more information regarding optical phase demodulation using an optical phase interferometric sensing arrangement such as arrangement 100, reference may be had to International Application Number PCT/US14/19232, entitled "Interferometric High Fidelity Optical Phase Demodulation" and filed Feb. 28, 2014.

It should be appreciated that the flow prediction techniques disclosed herein may be used with other sensing arrangements. For example, U.S. Pat. No. 7,764,363 and U.S. Pat. Pub. No. 2012/0067118 describe other sensing arrangements for which the disclosed flow prediction techniques may be used. In general, the disclosed flow prediction techniques may be applied to any distributed sensing system or sensor-based system where phase modulation and phase demodulation is used to track acoustic activity along an optical fiber. Further, in some embodiments, flow prediction based on acoustic activity and proppant compensation as described herein, may be modified to account for other sensor-based or distributed sensing parameters such as strain, vibrations, etc.

Figure 3:
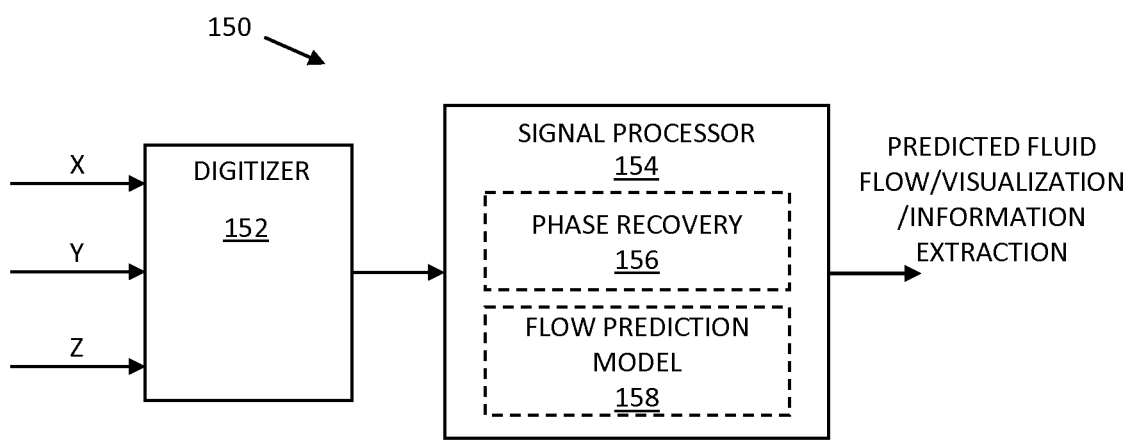
FIG. 3 is a block diagram of an illustrative signal processing arrangement.

FIG. 3 shows an illustrative signal processing arrangement 150 having a digitizer 152 that digitizes signals such as X, Y, Z, and signal processor 154 that receives the digitized signals from the digitizer 152. In accordance with at least some embodiments, the signal processor 154 comprises a phase recovery module 156 (e.g., to perform quadrature demodulation of phase) and a flow prediction module 158. For example, the signal processor 154 may correspond to one or more central processing unit (CPUs) or application-specific integrated circuits (ASICs) that execute software or firmware instructions corresponding to phase recovery module 156 and flow prediction module 158. The output of the signal processor 154 corresponds to predicted fluid flow results that can be stored, visualized, correlated with other parameters, and/or used for other information extraction. Further, the predicted fluid flow results can be used to make decisions regarding downhole operations involving proppants, diverters, treatments, and/or fracturing.

In some embodiments, at least some of the components represented in arrangements 100 and 150 may be implemented with surface interface 66 (FIGS. 1A-1C) and/or computer 70 of FIG. 1A. As an example, the laser 102, pulser 106, and first circulator 108 of FIG. 2 may be part of an interrogator included with surface interface 66. Further, the receiver 132, and α and β paths may correspond to receiver or interferometry components included with surface interface 66. Further, the digitizer 152 may be included with surface interface 66. Meanwhile, the signal processor 154 may be part of surface interface 66 or computer 70.

In at least some embodiments, the signal processor 154 executes instructions corresponding to phase recovery module 156 to obtain phase data correlated with acoustic activity along an optical fiber such as optical fiber 44 or 104. Acoustic activity values corresponding to the recovered phase data are provided as input to the flow prediction model 158. The flow prediction model 158 corresponds to one or more prediction models that correlate acoustic activity values and a proppant compensation value or factor with a fluid flow rate. There are various options for selecting flow prediction model 158, calibrating flow prediction model 158, and providing/adjusting inputs to flow prediction model 158. These various options can be implemented based on criteria such as the availability of data, the number of perforation clusters to be monitored, user preference, and/or other criteria. User input for the various options may be received, for example, via a graphical user interface.

With regard to selecting flow prediction model 158, a correlation between flow rate at a perforation cluster and acoustic activity is assumed. In at least some embodiments, the correlation between flow rate at a perforation cluster and acoustic activity is assumed to be a power law. In other words, if y is the flow rate through a perforation cluster and x is the acoustic activity, at least part of the flow prediction model 158 can be expressed as:

$$y=ax^{1/2}+b \text{(simplified power law model)}, \quad \text{[Equation 1]}$$

where a and b are predetermined constants. Another power law model example that may be used as at least part of flow prediction model 158 can be expressed as:

$$y=cx^n+d \text{(power law model)} \quad \text{[Equation 2]}$$

where c, n, and d are predetermined constants.
Meanwhile, a linear model that may be used as at least part of flow prediction model 158 can be expressed as:

$$y=ex+f \text{(linear model)}, \quad \text{[Equation 3]}$$

where e and f are predetermined constants.
Further, a logarithmic model that may be used as at least part of flow prediction model 158 can be expressed as:

$$y=g\log(x)+h \text{(logarithmic model)}, \quad \text{[Equation 4]}$$

where g and h are predetermined constants.

In at least some embodiments, the power law model of equation 2 is selected for use with flow prediction model 158 if only one perforation cluster is to be monitored. The prediction model 158 is then used on other stages of the well, which may have multiple perforation clusters or a single cluster. Alternatively, the power law model of equation 2 may be selected for use with flow prediction model 158 if n is known from previous experience (e.g., from similar wells using the same types of fluids). If n cannot be determined, the logarithmic model of equation 4 may be selected for use with flow prediction model 158. The simplified power law model of equation 1 and the linear model of equation 3 are options for flow prediction model 158 that may be selected if simplicity is favored over accuracy. Further, the different models corresponding to equations 1-4 could be combined such that an average or weighted average of two or more of the models are used with flow prediction model 158. For scenarios where a single perforation cluster is to be monitored, any of the models given in equations 1-4 may be used to represent flow for a single perforation cluster. To determine flow for a plurality of perforation clusters, individual flows predicted by the flow prediction model 158 are summed together.

In at least some embodiments, the flow prediction model 158 is calibrated. For example, the calibration may correspond to fitting or optimizing model parameters using a known flow rate (e.g., the surface flow input to a well) before proppants are added. More specifically, the predetermined constants (a, b, c, d, e, f, g, h) may correspond to model parameters that are selected based on such a calibration. In some cases, model calibration operations involve time-synchronizing acoustic activity values with a surface flow. As needed, the acoustic activity data and surface flow data can be averaged. Further, model calibration operations may be performed for one perforation cluster or multiple perforation clusters. Model calibration operations may additionally or alternatively include adjusting the flow prediction model 158 based on a comparison of acoustic activity values obtained with and without a surface fluid flow. Further, model calibration operations may additionally or alternatively include adjusting the flow prediction model 158 based on a comparison of acoustic activity values obtained with and without proppants being added to a fluid flow.

In accordance with at least some embodiments, the flow prediction model 158 also includes a proppant compensation factor or value. For simplicity, the proppant compensation factor or value may assume the same proppant concentration for all perforation clusters. Alternatively, to the extent acoustic activity values are available; the effect of proppants at different perforation clusters can be monitored and used to refine the proppant compensation factor or value for different perforation clusters.

In at least some embodiments, a flow prediction model 158 with proppant compensation is given as:

$$\hat{y}_n = \hat{y}_n + g \cdot p_n \quad \text{[Equation 5]}$$

where $\hat{y}_n$ is the predicted flow with proppant compensation at time index n, $y_n$ is the estimated flow without proppant compensation at time n (e.g., obtained from one of the models corresponding to equations 1-4), $p_n$ is a proppant concentration estimate for a measured depth at time n, and g is an optimization factor. The model of equation 5 responds instantaneously to changes in the estimated proppant concentration for a particular measured depth. Another flow prediction model 158 with proppant compensation is given as:

$$\hat{y} = y_n(1 + g \cdot g \cdot \bar{p}_n^{-d}) \quad \text{[Equation 6]}$$

where, $\hat{y}_n$ is the estimated flow with the proppant correction factor at time index n, and $y_n$ is the estimated flow without proppant compensation at time n (e.g., obtained from one of the models corresponding to equations 1-4). Further, $\bar{p}_n$ may be given as:

$$\bar{p}_n = p_n + \lambda \bar{p}_{n-1} \quad \text{[Equation 7]}$$

where $p_n$ is the estimated proppant concentration for a particular measured depth at time n, and $\lambda$, d, and g are obtained by optimization or fitting operations.

The example models described in equations 1-7 related to flow prediction model 158 are examples only. Other models may be developed. In general, contemplated flow prediction models correlate acoustic activity with fluid flow and compensate for proppants. In addition, flow prediction model 158 may adjust predicted flow based on parameters such as temperature, viscosity, measured depth, pressure, etc. While the model fitting operations described herein are intended to account for variations that are not wholly accounted for by acoustic activity values and the proppant compensation factor or value, it should be appreciated that some models may have more or less parameters. Further, it should be appreciated that the fit between predicted flow and a known flow rate may vary for different models.

In at least some embodiments, the inputs provided to the flow prediction model 158 changes how the predicted flow output from the flow prediction model 158 should be interpreted. For example, the acoustic activity values provided as input to the flow prediction model 158 may be averaged based on a predetermined spacing or timing criteria. In such case, the output of the flow prediction model 158 represents an averaged output. As an example, the acoustic activity values may correspond to acoustic activity averaged for 10 foot segments and 30 second intervals. Alternatively, the acoustic activity values may correspond to acoustic activity averaged for 30 foot segments and 10 second or 1 minute intervals. Further, the acoustic activity values input to the flow prediction model 158 may be normalized. For example, the normalization may be based on a noise-floor identified for at least one perforation cluster (e.g., when there is no fluid flow).

Further, the acoustic activity values input to the flow prediction model 158 may vary with regard to frequency band. In some embodiments, the acoustic activity values input to the flow prediction model 158 correspond to select frequency bands whose energy or intensity is being monitored. In at least some embodiments, deriving acoustic activity values to be input to the flow prediction model 158 may involve calculating phase energy for each of a limited number of frequency sub-bands of a distributed acoustic sensing signal obtained from each digitized electrical signal (see FIGS. 2 and 3). For more information regarding energy spectrum analysis techniques that could be used to obtain acoustic activity values for select frequency bands, reference may be had to application no. PCT/US2014/047141, entitled "Distributed Sensing Systems and Methods with Efficient Energy Spectrum Analysis", and filed Jul. 18, 2014.

In accordance with at least some embodiments, the acoustic activity values input to the flow prediction model 158 are assumed to represent actual acoustic signal without any artifacts from the sensor itself or from whatever modulation scheme is employed. The removal of modulation/demodulation artifacts is possible, for example, using appropriate filters.

In at least some embodiments, acoustic activity values are approximated by the root mean square (RMS) or standard deviation (STD) of a signal while the signal power is measured in time blocks chosen by the user. Thus, while acoustic activity data may be collected at 10,000 samples per second or higher, plotted acoustic activity values may be binned into large time blocks (e.g., time blocks of 10 seconds to several minutes are contemplated). Acoustic activity values plotted as a function of time and channel are sometimes referred to herein as a waterfall plot.

As an example, one channel of an acoustic activity plot may correspond to a one meter section of a borehole. For comparison, a perforation cluster is usually less than half a meter in length. As a result, DAS systems have poor spatial resolution such that acoustic activity at one point along an optical fiber is sensed at several channels. In practice, the spatial resolution will be determined by the DAS interrogation unit's compensation coil. An example compensation coil used for DAS monitoring of hydraulic fracturing provides a spatial resolution of around 10 meters. In such case, acoustic activity at one perforation cluster will be detected at 10 channels or along 10 meters of fiber. In different embodiments, the positioning of plotted acoustic activity values may be selected by a user or possibly by plotting software using predetermined criteria for interpreting acoustic activity data at multiple channels and/or the known position of perforation clusters based on well design specifications.

Figure 4:
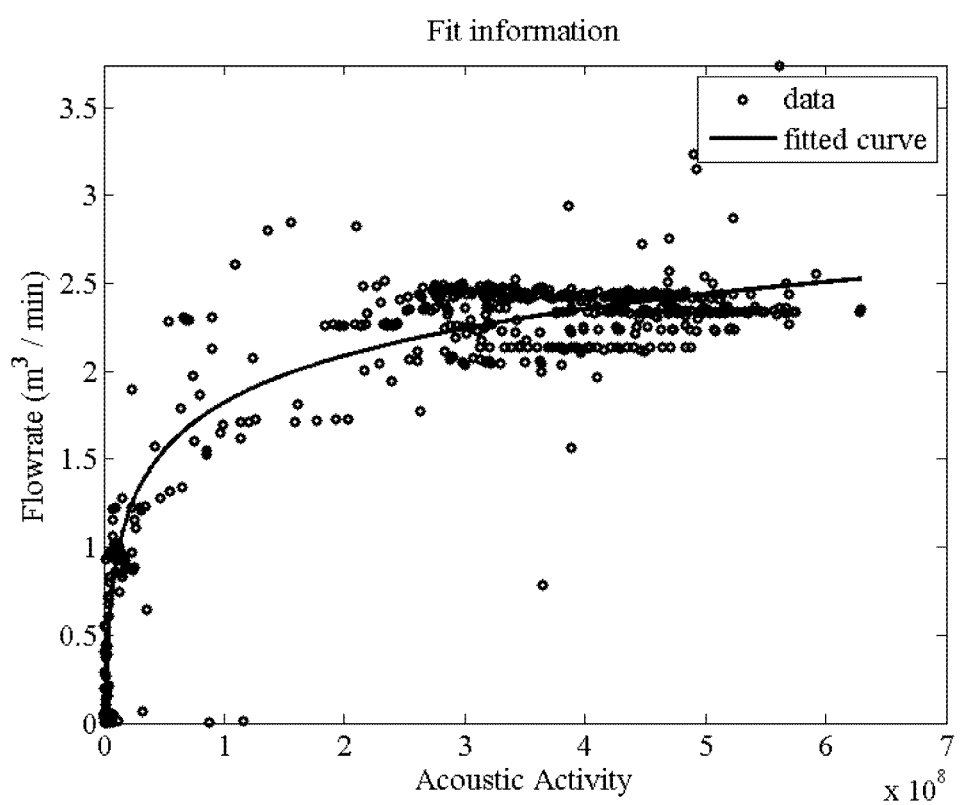
FIG. 4 is a graph showing flow rate as a function of acoustic activity.

FIG. 4 is a graph representing the relationship between flow rate and acoustic activity determined for a single wellbore stage with one perforation cluster. The relationship represented in FIG. 4 can be estimated as a power-law fit which deviates slightly from the reciprocal of the square root of the power of the signal. In at least some embodiments, graphs or fitted curves such as the fitted curve shown in FIG. 4 can be used to develop or adjust flow prediction model 158.

Figure 5A:
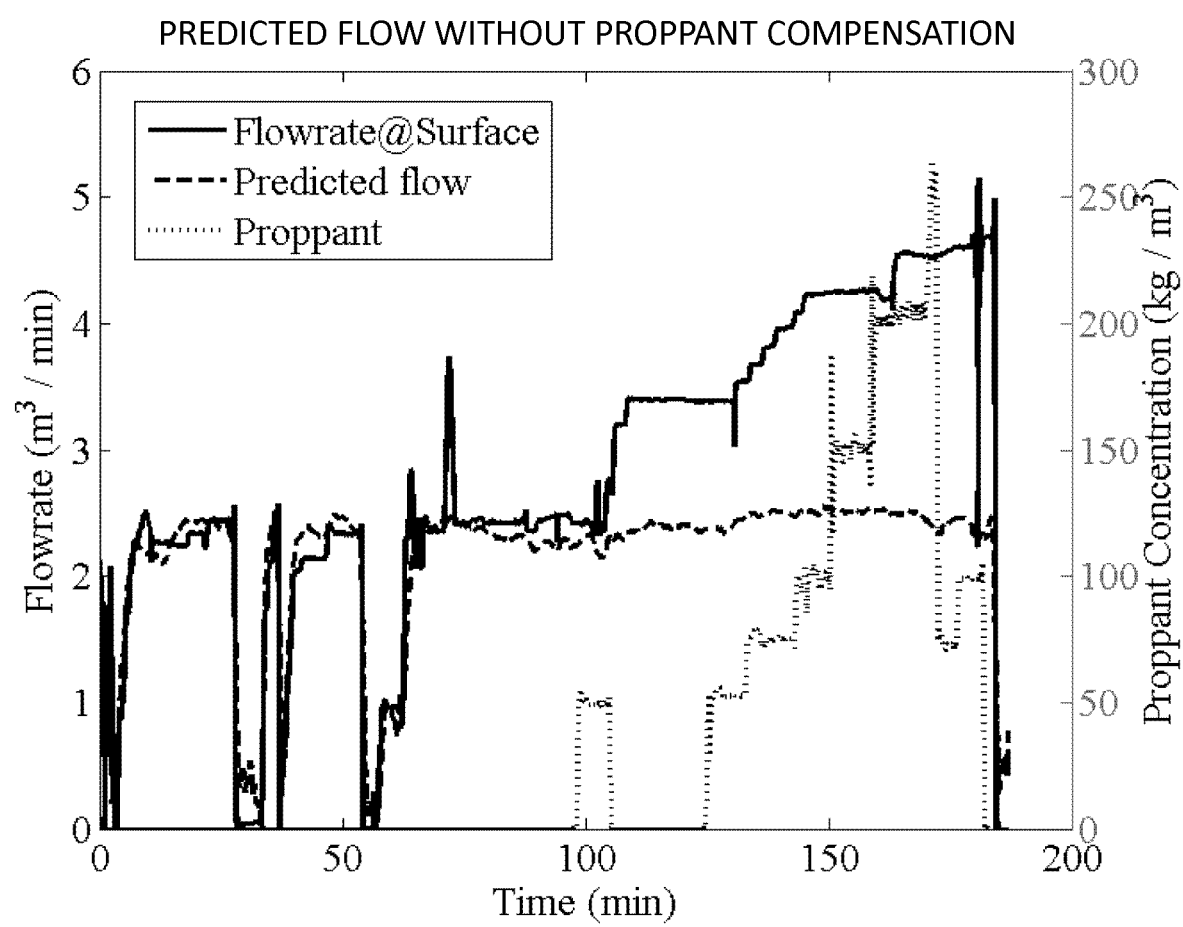
FIGS. 5A and 5B are graphs showing predicted and actual flow rates as a function of time.
Figure 5B:
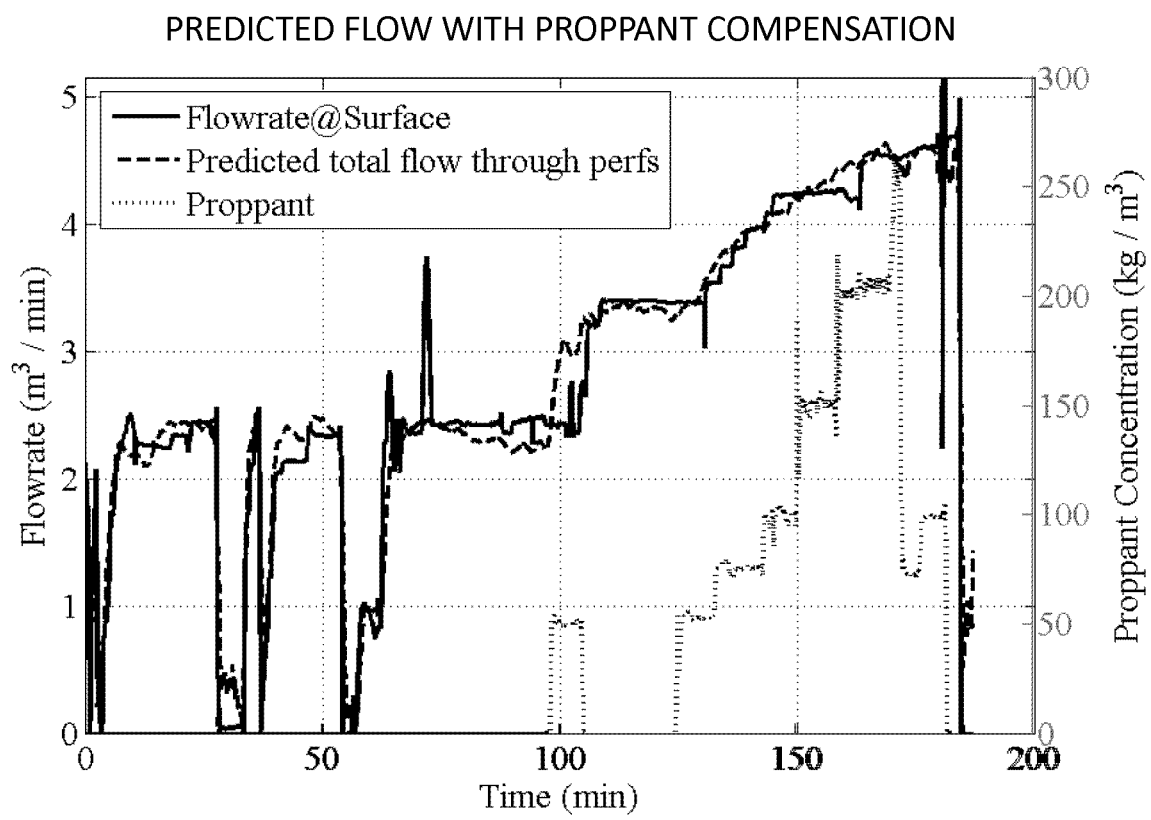

FIG. 5A compares surface flow rate, predicted fluid flow without proppant compensation, and proppant concentration as a function of time. In FIG. 5A, flow prediction without proppant compensation tracks a surface flow rate closely until proppants are added. Once proppants are added, fluid flow prediction without proppant compensation varies from the surface flow rate by a large margin FIG. 5B compares surface flow rate, predicted fluid flow with proppant compensation, and proppant concentration as a function of time. The surface flow rate and proppant concentration represented in FIG. 5B is the same as the surface flow rate and proppant concentration represented in FIG. 5A. As shown in FIG. 5B, predicted fluid flow with proppant compensation closely tracks the surface flow rate even after proppants are added. The predicted fluid flow with proppant compensation represented in FIG. 5B corresponds to the output from flow prediction model 158 for a single perforation cluster, where all the surface fluid flows to one perforation cluster. Alternatively, the predicted flow with proppant compensation represented in FIG. 5B may correspond to a sum of predicted fluid flows output from flow prediction model 158, where each predicted fluid flow corresponds to a different perforation cluster.

Figure 6A:
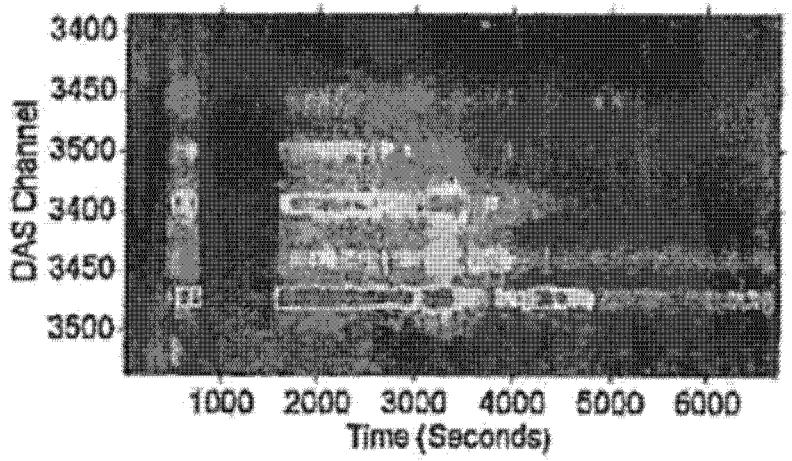
FIG. 6A is a graph showing acoustic activity values as a function of time and measured depth.

FIG. 6A shows an example acoustic activity plot or "waterfall plot" representing acoustic activity as a function of time for several perforation clusters. Plots such as the one shown in FIG. 6A may be derived from acoustic activity data collected from a DAS system and/or other downhole sensors. In FIG. 6A, the plotted data moves from left to right as a function of time. In FIG. 6A, most of the acoustic activity occurs between 1500 seconds to 3500 seconds. The attenuation of acoustic activity after 3500 seconds is due to the addition of proppants.

Figure 6B:
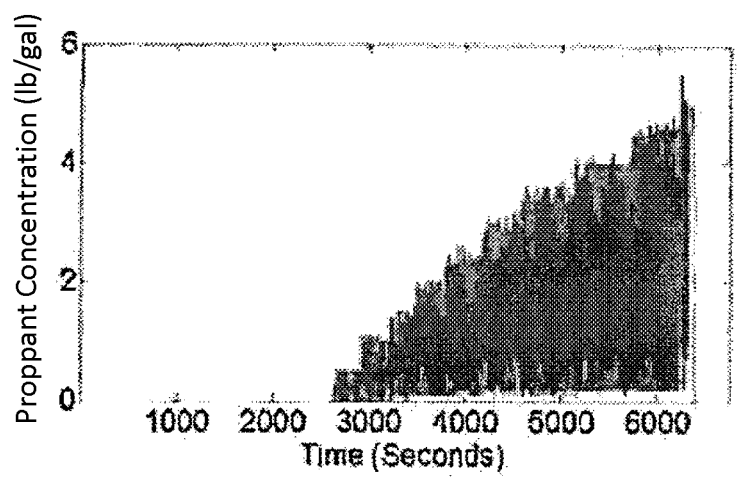
FIG. 6B is a graph showing proppant concentration as a function of time.

FIG. 6B shows a graph representing proppant concentration as a function of time. As shown in FIG. 6B, proppant is added around 2700 seconds and the proppant concentration increases thereafter. Again, the acoustic activity attenuation represented in FIG. 6A after 3500 seconds is due to the rising proppant compensation represented in FIG. 6B after 2700 seconds.

Figure 6C:
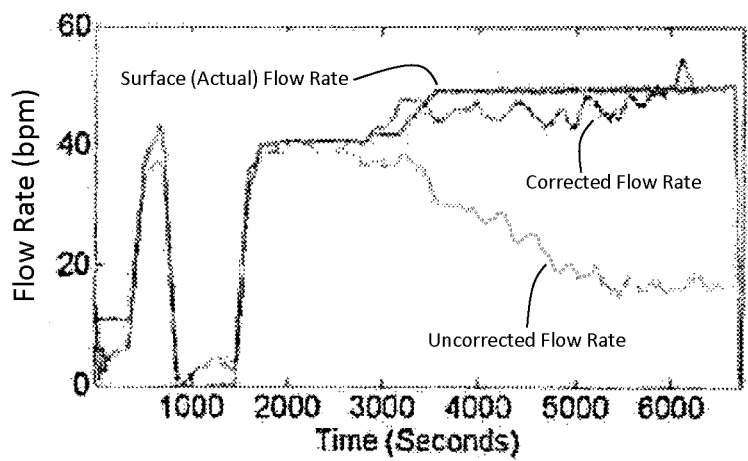
FIG. 6C is a graph showing flow rates as a function of time.

FIG. 6C shows a plot of three curves representing a "surface flow rate", a "corrected flow rate", and an "uncorrected flow rate." The surface flow rate curve represents an actual surface flow rate as a function of time. The uncorrected flow rate curve represents a fluid flow as a function of time estimated using acoustic activity data without proppant compensation. The corrected flow rate curve represents a predicted fluid flow as a function of time obtained using acoustic activity data and a proppant compensation factor or value (to account for the attenuation of acoustic activity caused by proppants as described herein). In at least some embodiments, the corrected flow rate curve corresponds to a fluid flow prediction obtained from flow prediction model 158 as described herein.

Figure 7:
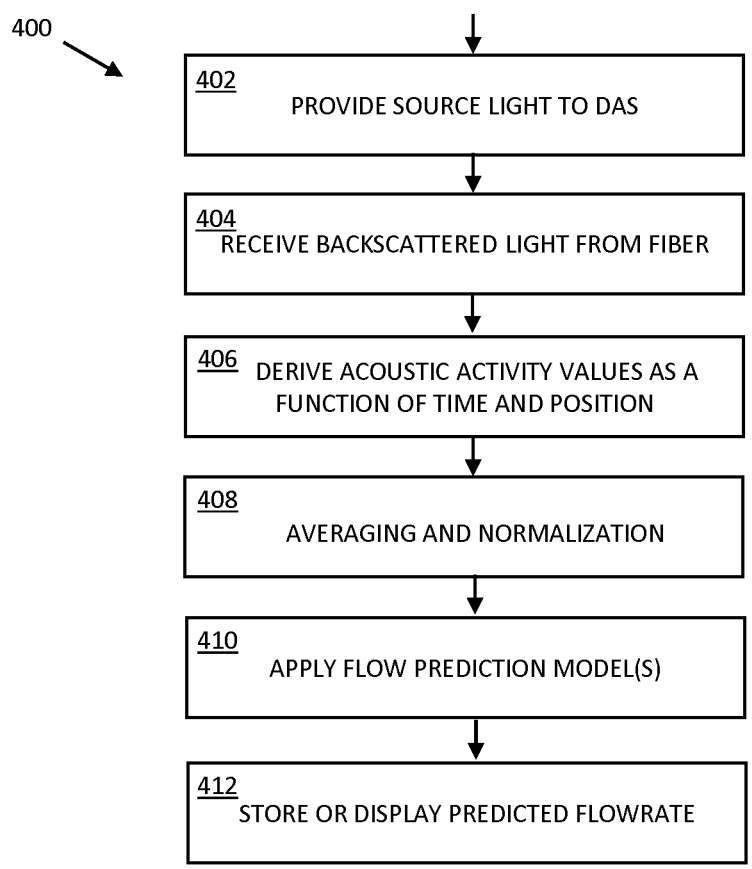
FIG. 7 is a flowchart showing of an illustrative flow prediction method.

FIG. 7 is a block diagram of a flow prediction method 400. As shown, the method 400 includes providing source light to an optical fiber (e.g., fiber 44 or 104) at block 402. At block 404, backscattered light is received from the optical fiber. At block 406, acoustic activity values are derived as a function of time and position using the backscattered light received at block 404. For example, an optical phase interferometric sensing arrangement such as arrangement 100 (FIG. 2) and processing arrangement such as arrangement 150 may derive the acoustic activity values as described herein. In at least some embodiments, the acoustic activity values are averaged and/or normalized at block 408. At block 410, one or more flow prediction models are applied to predict flow using acoustic activity values obtained from blocks 406 or 408. The flow prediction model or models applied at block 410 also use a proppant compensation factor or value as described herein. At block 412, the predicted flow rate output from the flow prediction model of block 410 is stored or displayed. As an example, the predicted flow rate of block 412 may be used for turbulent flow monitoring, plug leak detection, flow-regime determination, wellbore integrity monitoring, event detection, data visualization, and decision making. In some embodiments, a computer system displays a plan based on the predicted fluid flow of block 412. The plan may correspond to well treatment operations or proppant injection operations. Additionally or alternatively, a computer system may generate control signals to initiate or adjust a downhole operation based on the predicted fluid flow of block 412. Example downhole operations include, for example, well treatment operations (acidization), proppant injection operations, and fracturing operations.

Embodiments disclosed herein include:

A: a method, comprising obtaining distributed measurements of acoustic energy as a function of time and position downhole; deriving acoustic activity values as a function of time and position from the one or more distributed measurements; applying at least some of the acoustic activity values to a flow prediction model to obtain a predicted fluid flow for a downhole perforation cluster as a function of time, wherein the flow prediction model includes a proppant compensation value or factor; and storing or displaying the predicted fluid flow.

B: a system, comprising an optical fiber; a light source to provide source light to the optical fiber; a receiver coupled to the optical fiber, wherein the receiver comprises: at least one optical fiber coupler that receives backscattered light and that produces one or more optical interferometry signals from the backscattered light; and photo-detectors that produce an electrical signal for each of the one or more optical interferometry signals; at least one digitizer that digitizes each electrical signal to obtain one or more digitized electrical signals; and at least one processing unit that processes the one or more digitized electrical signal to obtain acoustic activity values as a function of time and position, wherein the at least one processing unit applies at least some of the acoustic activity values to a flow prediction model to obtain a predicted fluid flow for a downhole perforation cluster as a function of time, and wherein the flow prediction model includes a proppant compensation value or factor.

Each of embodiments A and B may have one or more of the following additional elements in any combination: Element 1: wherein the distributed measurements are derived from providing source light to an optical fiber deployed in a downhole environment; receiving backscattered light from the optical fiber and producing one or more optical interferometry signals from the backscattered light; and converting each of the one or more optical interferometry signals to an electrical signal and digitizing each electrical signal to obtain one or more digitized electrical signals. Element 2: further comprising applying at least some of the acoustic activity values to the flow prediction model to obtain a predicted fluid flow for each of a plurality of perforation clusters. Element 3: further comprising calibrating the flow prediction model based on a comparison of a sum of predicted fluid flow for each of at least one perforation cluster and a surface fluid flow without proppants. Element 4: further comprising calibrating the flow prediction model based on a comparison of acoustic activity values obtained with and without a surface fluid flow. Element 5: further comprising calibrating the flow prediction model based on a comparison of acoustic activity values obtained with and without proppant. Element 6: further comprising averaging acoustic activity values input to the flow prediction model in accordance with a predetermined spacing or timing criteria. Element 7: further comprising normalizing acoustic activity values input to the flow prediction model based on a noise-floor identified for at least one perforation cluster. Element 8: wherein deriving the acoustic activity values comprises calculating phase energy for each of a limited number of frequency sub-bands of a distributed acoustic sensing signal obtained from each digitized electrical signal. Element 9: wherein the proppant compensation factor or value is a function of a downhole proppant estimate. Element 10: wherein the proppant compensation factor or value is a function of an acoustic attenuation estimate. Element 11: further comprising displaying a plan based on the predicted fluid flow, the plan related to at least one of well treatment operations and proppant injection operations. Element 12: further comprising initiating or adjusting a downhole operation based on the predicted fluid flow, the downhole operation related to at least one of well treatment operations or proppant injection operations. Element 13: wherein the at least one processing unit applies at least some of the acoustic activity values to the flow prediction model to obtain a predicted fluid flow for each of at least one perforation cluster. Element 14: wherein the at least one processing unit calibrates the flow prediction model based on at least one comparison selected from the list consisting of a comparison of a sum of predicted fluid flow for each of at least one perforation cluster and a surface flow rate, a comparison of acoustic activity values obtained with and without a surface fluid flow, and a comparison of acoustic activity values obtained before and after proppant is added. Element 15: wherein the at least one processing unit modifies acoustic activity values input to the flow prediction model based on at least one operation selected from the list consisting of averaging acoustic activity values in accordance with a predetermined spacing or timing criteria and normalizing acoustic activity values based on a noise-floor value identified for at least one perforation cluster. Element 16: wherein the at least one processing unit adjusts the proppant compensation factor or value as a function of a downhole proppant estimate or an acoustic attenuation estimate. Element 17: further comprising a monitor in communication with the at least one processing unit, wherein the at least one processing unit causes the monitor to display a plan based on the predicted fluid flow, the plan related to at least one of well treatment operations and proppant injection operations. Element 18: wherein the at least one processing unit provides a control signal to initiate or adjust a downhole operation based on the predicted fluid flow, the downhole operation related to at least one of well treatment operations and proppant injection operations.

Numerous variations and modifications will become apparent to those skilled in the art once the above disclosure is fully appreciated. For example, flow prediction models such as any of the models disclosed herein may be extended or varied for different fluid types and proppant types as well as wellbore completion types. It is intended that the following claims be interpreted to embrace all such variations and modifications.

What is claimed is:

1. A method, comprising:
    measuring, by photodetectors over time, acoustic energy correlated with fluid flow at a downhole perforation cluster and at different positions downhole based on interferometric sensing of backscatter of a pulsed interrogation signal in an optical fiber arranged downhole in a formation, the pulsed interrogation signal associated with a light source;
    deriving acoustic activity values correlated with the fluid flow at the downhole perforation cluster as a function of time and position from the acoustic energy measurements;
    applying at least some of the acoustic activity values to a flow prediction model to obtain a proppant compensated fluid flow rate for the downhole perforation cluster as a function of time, wherein the flow prediction model includes a proppant compensation value or factor, wherein at least a portion of the flow prediction model indicates a fluid flow rate at the downhole perforation cluster based on the acoustic activity values correlated with the fluid flow at the downhole perforation cluster, and another portion of the flow prediction model indicates the proppant compensation value or factor based on a function of a proppant concentration estimate, wherein the flow prediction model is a sum of the fluid flow rate at the downhole perforation cluster and the proppant compensation value; and
    adjusting proppant injection operations by diverting flow with respect to perforation clusters based on the proppant compensated fluid flow rate;
        wherein the at least the portion of the flow prediction model comprises calculating the fluid flow rate as a sum of (i) a first constant multiplied by one or more of the acoustic activity values raised to a power and (ii) a second constant.

2. The method of claim 1, wherein said measuring acoustic energy comprises:
    providing source light to an optical fiber deployed in a downhole environment;
    receiving backscattered light from the optical fiber and producing one or more optical interferometry signals from the backscattered light; and
    converting each of the one or more optical interferometry signals to an electrical signal and digitizing each electrical signal to obtain one or more digitized electrical signals.

3. The method of claim 2, wherein deriving the acoustic activity values comprises calculating phase energy for each of a limited number of frequency sub-bands of a distributed acoustic sensing signal obtained from each digitized electrical signal.

4. The method of claim 1, further comprising applying at least some of the acoustic activity values to the flow prediction model to obtain a proppant compensated fluid flow rate for each of a plurality of perforation clusters.

5. The method of claim 1, further comprising calibrating the flow prediction model based on a comparison of a sum of proppant compensated fluid flow rates for each of at least one perforation cluster and a surface fluid flow rate without proppants.

6. The method of claim 1, further comprising calibrating the flow prediction model based on a comparison of acoustic activity values obtained with and without a surface fluid flow.

7. The method of claim 1, further comprising calibrating the flow prediction model based on a comparison of acoustic activity values obtained for fluid with and without proppant.

8. The method of claim 1, further comprising averaging acoustic activity values input to the flow prediction model in accordance with a predetermined spacing or timing criteria.

9. The method of claim 1, further comprising normalizing acoustic activity values input to the flow prediction model based on a noise-floor identified for at least one perforation cluster.

10. The method of claim 1, wherein the proppant compensation factor or value is a function of a downhole proppant estimate.

11. The method of claim 1, wherein the proppant compensation factor or value is a function of an acoustic attenuation estimate.

12. The method of claim 1, further comprising displaying a plan based on the proppant compensated fluid flow, the plan related to at least one of well treatment operations and proppant injection operations.

13. The method of claim 1, further comprising initiating or adjusting a downhole operation based on the proppant compensated fluid flow rate, the downhole operation related to at least one of well treatment operations or proppant injection operations.

14. A system, comprising:
an optical fiber arranged downhole in a formation;
a light source to provide source light to the optical fiber;
a receiver coupled to the optical fiber, wherein the receiver comprises:
at least one optical fiber coupler that receives backscattered light from a pulsed interrogation signal associated with the light source and that produces one or more optical interferometry signals from the backscattered light; and
photo-detectors that produce an electrical signal for each of the one or more optical interferometry signals;
at least one digitizer that digitizes each electrical signal to obtain one or more digitized electrical signals; and
at least one processing unit configured to,
process the one or more digitized electrical signals to obtain acoustic activity values correlated with fluid flow at a downhole perforation cluster as a function of time and position, wherein the at least one processing unit applies at least some of the acoustic activity values correlated with the fluid flow at the downhole perforation cluster to a flow prediction model to obtain a proppant compensated fluid flow rate for the downhole perforation cluster as a function of time, wherein the flow prediction model includes a proppant compensation factor, and wherein at least a portion of the flow prediction model indicates a fluid flow rate at the downhole perforation cluster based on the acoustic activity values correlated with the fluid flow at the downhole perforation cluster, and another portion of the flow prediction model indicates the proppant compensation factor based on a function of a proppant compensation estimate, wherein the flow prediction model is a sum of the fluid flow rate at the downhole perforation cluster and the proppant compensation value; and
adjust proppant injection operations by diverting flow with respect to perforation clusters based on the proppant compensated fluid flow rate;
wherein the at least the portion of the flow prediction model comprises calculating the fluid flow rate as a sum of (i) a first constant multiplied by one or more of the acoustic activity values raised to a power and (ii) a second constant.

15. The system of claim 14, wherein the at least one processing unit applies at least some of the acoustic activity values to the flow prediction model to obtain a proppant compensated fluid flow rate for each of at least one perforation cluster.

16. The system of claim 14, wherein the at least one processing unit calibrates the flow prediction model based on a comparison of a sum of proppant compensated fluid flow rates for each of at least one perforation cluster and a surface flow rate.

17. The system of claim 14, wherein the at least one processing unit modifies acoustic activity values input to the flow prediction model based on at least one operation selected from a list consisting of averaging acoustic activity values in accordance with a predetermined spacing or timing criteria and normalizing acoustic activity values based on a noise-floor value identified for at least one perforation cluster.

18. The system of claim 14, wherein the at least one processing unit adjusts the proppant compensation factor as a function of a downhole proppant estimate or an acoustic attenuation estimate.

19. The system of claim 14, further comprising a monitor in communication with the at least one processing unit, wherein the at least one processing unit causes the monitor to display a plan based on the proppant compensated fluid flow rate, the plan related to at least one of well treatment operations and proppant injection operations.

20. The system of claim 14, wherein the at least one processing unit provides a control signal to initiate or adjust a downhole operation based on the proppant compensated fluid flow rate, the downhole operation related to at least one of well treatment operations and proppant injection operations.

* * * * *